United States Patent [19]

Kaule

[11] 4,388,832
[45] Jun. 21, 1983

[54] METHOD AND APPARATUS FOR RECEIVING ULTRASONIC WAVES BY OPTICAL MEANS

[75] Inventor: Walter Kaule, Cologne, Fed. Rep. of Germany

[73] Assignee: Krautkramer-Branson, Inc., Stratford, Conn.

[21] Appl. No.: 279,606

[22] Filed: Jul. 1, 1981

[30] Foreign Application Priority Data

Aug. 6, 1980 [DE] Fed. Rep. of Germany ....... 3029776

[51] Int. Cl.³ ............................................. G01N 29/00
[52] U.S. Cl. ..................................................... 73/655
[58] Field of Search ........................... 73/655, 656, 657

[56] References Cited

U.S. PATENT DOCUMENTS 3,355,934 12/1967 Foster .................................. 73/657
4,265,122 5/1981 Cook et al. .......................... 73/655
4,345,475 8/1982 Bickel .................................. 73/655

*Primary Examiner*—Anthony V. Ciarlante
*Attorney, Agent, or Firm*—Ervin B. Steinberg; Philip J. Feig

[57] ABSTRACT

In an apparatus for receiving ultrasonic waves by optical means a laser beam illuminates a workpiece surface at which ultrasonic waves are manifest in the form of cyclically occurring surface deformations. The reflected light is transmitted to an optical interferometer as a measuring light beam and the beam exiting from the interferometer is converted to an electrical signal and amplified to provide a measuring beam responsive electrical signal. A portion of the laser beam immediately before being incident on the workpiece surface is also passed through the interferometer as a comparison beam. The exiting comparison beam light is converted to an electrical signal, amplified and time delayed to provide a comparison beam responsive electrical signal. By means of a subtracting circuit the comparison beam responsive electrical signal is subtracted from the measuring beam responsive electrical signal to provide a difference signal which is evaluated. The time delay is adjusted to cause the difference signal to be free of the frequency and amplitude responsive variations of the laser beam. In a Michelson type interferometer both light beams traverse the same paths in the same direction, but spatially separated. In a Mach-Zehnder interferometer both light beams traverse the same paths in respective opposite directions.

8 Claims, 2 Drawing Figures

METHOD AND APPARATUS FOR RECEIVING ULTRASONIC WAVES BY OPTICAL MEANS

BRIEF SUMMARY OF THE INVENTION

This invention refers to a method and apparatus for receiving by optical means ultrasonic waves manifest on the surface of a workpiece to be tested by illuminating, by means of a laser light, the workpiece surface portion which undergoes physical deflection in time with the period of the ultrasonic wave, and demodulating by the use of a transit time interferometer the light used for measuring such deflections, which light has been modulated by the surface deflections.

When an ultrasonic wave is produced in a workpiece which is to be examined by ultrasonic energy, the propagation of the ultrasonic wave within the workpiece is disturbed at locations which exhibit different acoustic properties from the surrounding area. Such locations may, for example, be characterized by inclusions of foreign matter, separation of the material, structural changes, and so on. The surface of the workpiece to be examined will exhibit an ultrasonic wave pattern which contains information about the inner structure of the workpiece. It is known to scan this ultrasonic wave pattern by means of electroacoustic transducers which convert the pattern to electrical signal voltages, and then to evaluate the pattern from the shape of these voltages or their amplitudes as a function of time. Contactless optical methods which use optical interferometer systems are also known for scanning ultrasonic wave patterns, see Ultrasonic Testing of Materials, 2nd edition, by J. and H. Krautkramer, Springer Verlag, New York, New York (1977), pp. 165 to 172. In these methods the surface of the workpiece from which the ultrasonic waves are to be received is illuminated with monochromatic light, for instance a laser beam which frequently is a frequency-stabilized single mode laser. The laser light is scattered or reflected at the surface of the workpiece and the reflected or scattered light is frequency modulated responsive to the Doppler effect arising from the ultrasonic deflections of the workpiece surface. This frequency modulation is converted to brightness fluctuations (amplitude modulation) by interferometer devices and converted into electrical signal voltages by means of photoelectric means. These voltages are then displayed, for example on a cathode ray oscilloscope, and used for evaluation.

In an interferometer system of the type indicated, the reflected light beam is generally split, passed through the interferometer over two different paths, and then combined. If the light beam along one of the optical paths is delayed by a time interval approximating one half the oscillation period of the ultrasonic wave, then darkness, maximum brightness or an average brightness can be obtained in the interferometer field of view after recombination of the two previously split beams. If the light entering the interferometer is modulated with the frequency of the ultrasonic wave, the brightness in the field of view of the interferometer will fluctuate at that frequency. Photoelectric means disposed will thus deliver an electrical signal voltage which per unit of time contains these brightness variations.

A disadvantage of the known methods referred to hereinabove is that the frequency and amplitude variations of the laser beam illuminating the workpiece result in corresponding brightness variations in the interferometer field of view and that these laser beam variations are superimposed on the brightness variations caused by the ultrasonic waves.

A principal object of this invention, therefore, is the provision of a method and apparatus of the type referred to above in which erroneous or ambiguous results of the measurement arising from the frequency and amplitude variations of the laser beam illuminating the workpiece surface are avoided to the greatest extent possible.

Other details and advantages of the present invention will be apparent from the embodiments described hereinafter with reference to the accompanying drawings.

DETAILED DESCRIPTION OF THE INVENTION

Figure 1:
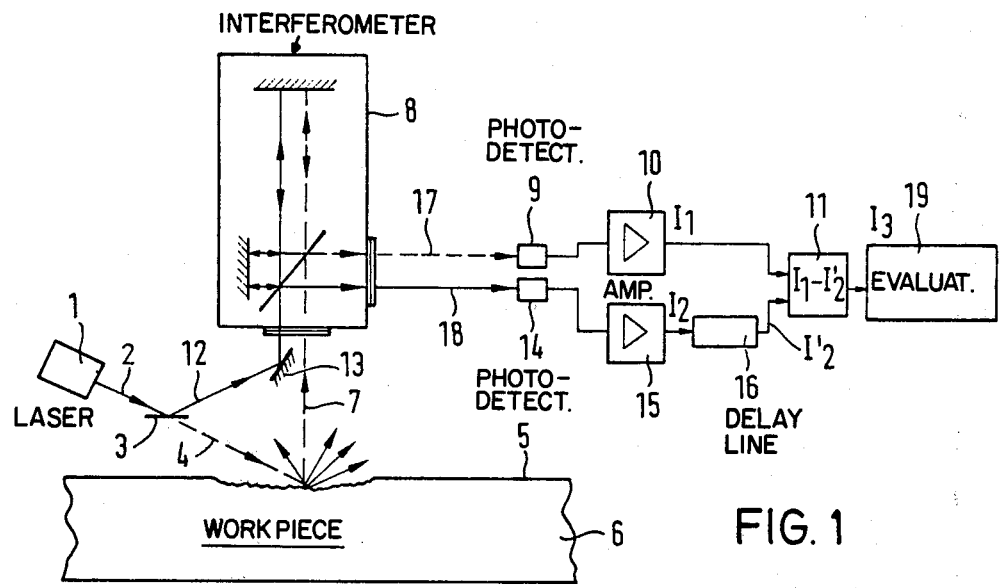
FIG. 1 is a schematic diagram of an apparatus showing a typical embodiment of the present invention.

FIG. 1 shows a laser 1, the beam of light 2 of which is transmitted toward a partially reflecting mirror 3. The portion 4 of the light which is transmitted through the mirror 3 (shown by the broken line) illuminates the surface 5 of the workpiece 6. The light 7 reflected and scattered at the surface 5 passes to a transit time interferometer 8, which is constructed as a Michelson interferometer in the example illustrated. The brightness-modulated light 17 obtained at the interferometer exit is received by a photodetector 9. The electrical signals obtained at the output of this detector 9 are amplified in an amplifier 10 and fed to a difference forming circuit 11.

The portion 12 of the light 2 produced by the laser 1 which is reflected from the mirror 3 also passes into the interferometer 8 via a reflecting mirror 13 and the corresponding brightness-modulated light 18 passes to a photodetector 14. The resulting electrical signals are also fed to the difference forming circuit 11 via an amplifier 15 and an electrical delay line 16. As shown in FIG. 1, the beams of light 12 and 7 traverse the same paths, parallel to one another, in the interferometer 8. The two beams are therefore spatially separated from one another.

The operation of the apparatus described is based essentially on the principle of eliminating undesirable brightness fluctuations, due to frequency and amplitude variations of the laser light 2, from the electrical signal values $I_1$ obtained at the output of the amplifier 10, and this is accomplished by forming a corresponding signal $I_2'$ and subtracting it from $I_1$. The value $I_2'$ must be responsive only to the frequency and amplitude fluctuations of the laser light 2, and not to the deflections of the surface 5 of the workpiece 6. The corresponding beam of light 12 used as a comparison beam is therefore taken out of the laser beam 2 by means of the mirror 3 before the laser beam strikes the surface 5. As a result, the comparison beam (12, 18) is somewhat shorter than the measuring beam (4, 7, 17). The signals at the output of the amplifiers 10 and 15, i.e. $I_1$ and $I_2$, therefore have different phases in respect of the signal variations caused by the frequency and amplitude variations. These phase differences of $I_1$ and $I_2$ are compensated by means of the delay line 16. Electrical signal $I_2'$ at the output end of the delay line 16 therefore has the same phase as the signal $I_1$. The signal $I_3 = I_1 - I_2'$ obtained at the output of the difference forming circuit 11 then has practically no fluctuations arising from the frequency and amplitude variations of the laser beam 2.

There are two advantages of taking the comparison beam 12, 18 through the interferometer 8: First of all, the optical paths of the comparison and measuring beams are not significantly different, so that all that is required is fine tuning by means of the delay line 16. On the other hand, and this is the more important factor, it is only by this step that it is possible electrically to compensate for frequency variations of the laser beam 2, for the interferometer converts these frequency variations into corresponding brightness, i.e. amplitude, variations which are then converted to corresponding signal variations by the photodetectors. And it is frequently precisely these measuring beam amplitude variations originating from frequency variations of the laser beam 2 that have to be compensated.

Figure 2:
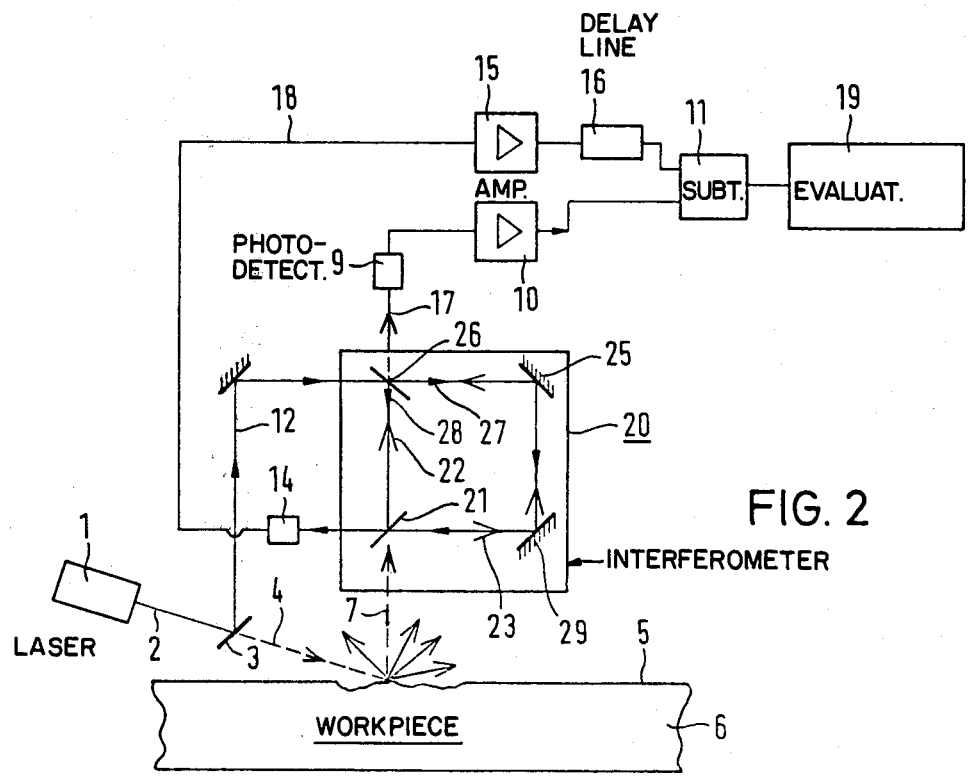
FIG. 2 is a schematic diagram illustrating an alternative embodiment utilizing a Mach-Zehnder interferometer.

The method described has proved particularly useful with interferometers of the Mach-Zehnder type, because in that case the measuring and comparison beams need not be taken through the interferometer in spatially separated relationship, with the consequent considerable adjustment problems. On the contrary, the two beams can traverse the same optical paths, provided the directions of the beams are in opposition to one another. This is shown in FIG. 2, in which the same reference numerals are used for parts of the apparatus shown in FIG. 1.

The measuring beam 7 (shown by an open arrowhead in FIG. 2) divides up into a light beam 22 and a light beam 23 at the interferometer mirror 21. After reflection of beam 23 at mirrors 29 and 25 the two beams are superimposed at the semi-reflecting mirror 26. The corresponding brightness variations are then converted to corresponding electrical signal variations by the photodetector 9.

The comparison beam 12 (shown by a closed arrowhead in FIG. 2), produced by the partially reflecting mirror 3, is divided by the mirror 26 into a beam 27 and a beam 28 which traverse the same optical paths as the beams 23 and 22, but in the opposite direction. Both beams 27 and 28 are superimposed at the semi-reflecting mirror 21 and the combined beams are transmitted to the photodetector 14. The electrical circuit, that is amplifier, delay line and subtraction circuit, is the same as has been described in connection with FIG. 1.

While there has been described and illustrated a preferred embodiment of the invention and a modification thereof, it will be apparent to those skilled in the art that various further modifications and changes may be made without deviating from the principle of the invention which shall be limited only by the scope of the appended claims.

What is claimed is:

1. The method of receiving ultrasonic waves from a workpiece by optical means wherein the ultrasonic waves are manifest as cyclic deformations occurring at a surface portion of the workpiece comprising:

providing a laser beam and causing it to be incident upon the surface portion to illuminate such portion;

transmitting the laser beam light reflected at said surface portion as a measuring beam to an optical interferometer and converting the optical signal responsive to said measuring beam after traversing said interferometer to a first electrical signal;

separating a portion from said laser beam before said beam is incident upon said workpiece surface portion;

transmitting said non-incident beam portion as a comparison beam to said optical interferometer and converting the optical signal responsive to said comparison beam after traversing said interferometer to a second electrical signal;

separately amplifying said first and said second electrical signals;

delaying said second amplified electrical signal;

subtracting said amplified and delayed second electrical signal from said amplified first electrical signal to provide a difference signal, and evaluating said difference signal.

2. The method of receiving ultrasonic waves from a workpiece as set forth in claim 1, said delay being selected to cause said difference signal to be substantially free of frequency and amplitude responsive fluctuations of said laser beam.

3. The method of receiving ultrasonic waves from a workpiece as set forth in claim 2, said measuring beam and said comparison beam traversing said interferometer spatially separated along the same optical path directions.

4. The method of receiving ultrasonic waves from a workpiece as set forth in claim 2, said interferometer being of the Mach-Zehnder type, said measuring beam and said comparison beam traversing said interferometer along the same optical paths but in respective opposite directions.

5. An apparatus for receiving ultrasonic waves from a workpiece by optical means, such waves being manifest as cyclic deformations occurring at a surface portion of the workpiece comprising:

a laser disposed for illuminating the surface portion with a beam of laser light;

an optical interferometer disposed for receiving the light reflected at said portion and said light traversing said interferometer as a measuring beam;

first photoelectric means disposed for receiving said measuring beam after traversing said interferometer and providing a first electrical signal;

means disposed for causing a portion of said laser light beam before it is incident upon said surface portion to also be received by said interferometer and traverse said interferometer as a comparison beam;

second photoelectric means disposed for receiving said comparison beam after traversing said interferometer and providing a second electrical signal;

amplifying means for separately amplifying said first electrical signal and said second electrical signal;

delay means coupled for receiving said second electrical signal and delaying said second signal;

difference means coupled for subtracting said second and delayed electrical signal from said first electrical signal to provide a difference signal, and evaluation means coupled for receiving said difference signal.

6. An apparatus for receiving ultrasonic waves as set forth in claim 5, said delay means being adjusted to cause said difference signal to be substantially free of frequency and amplitude responsive fluctuations of said beam of laser light.

7. An apparatus for receiving ultrasonic waves as set forth in claim 6, said measuring beam and said comparison beam traversing said interferometer spatially separated along substantially identical optical paths in the same direction.

8. An apparatus for receiving ultrasonic waves as set forth in claim 6, said interferometer being of the Mach-Zehnder type, said measuring beam and said comparison beam traversing said interferometer along substantially identical optical paths but in opposite directions with respect to one another.

* * * * *